(12) United States Patent
Stupak

(10) Patent No.: US 8,267,962 B2
(45) Date of Patent: Sep. 18, 2012

(54) DEVICE FOR REPOSITIONING CARTILAGE AND METHOD OF USE

(76) Inventor: Howard D. Stupak, Southport, CT (US)

( * ) Notice: Subject to any disclaimer, the term of this patent is extended or adjusted under 35 U.S.C. 154(b) by 724 days.

(21) Appl. No.: 12/313,599

(22) Filed: Nov. 21, 2008

(65) Prior Publication Data

US 2009/0143821 A1 Jun. 4, 2009

Related U.S. Application Data

(60) Provisional application No. 61/005,158, filed on Dec. 3, 2007, provisional application No. 61/011,026, filed on Jan. 14, 2008, provisional application No. 61/070,646, filed on Mar. 25, 2008.

(51) Int. Cl.
*A61B 17/04* (2006.01)
*A61F 2/18* (2006.01)
*A61M 29/00* (2006.01)
*A61B 17/06* (2006.01)

(52) U.S. Cl. .............. 606/232; 623/10; 606/199

(58) Field of Classification Search ........ 606/222, 606/228, 232, 199, 103, 233, 139, 144, 148; 623/10; 128/898, 200.24
See application file for complete search history.

(56) References Cited

U.S. PATENT DOCUMENTS

| | | | | |
|---|---|---|---|---|
| 3,570,497 A * | 3/1971 | Lemole | | 606/151 |
| 3,935,859 A | 2/1976 | Doyle | | |
| 4,031,569 A * | 6/1977 | Jacob | | 623/10 |
| 4,938,234 A * | 7/1990 | Capriotti | | 128/898 |
| 5,112,353 A * | 5/1992 | Johansson et al. | | 623/10 |
| 5,219,359 A * | 6/1993 | McQuilkin et al. | | 606/232 |
| 5,312,436 A | 5/1994 | Coffey et al. | | |
| 5,403,346 A * | 4/1995 | Loeser | | 606/228 |
| 5,533,499 A * | 7/1996 | Johnson | | 128/200.24 |
| 5,632,753 A * | 5/1997 | Loeser | | 606/151 |
| 5,706,800 A | 1/1998 | Cronk et al. | | |
| 5,716,405 A * | 2/1998 | Mittelman | | 623/10 |
| 5,931,799 A | 8/1999 | Guastella et al. | | |
| 6,106,541 A | 8/2000 | Hurbis | | |
| 6,186,965 B1 | 2/2001 | Patterson | | |
| 6,244,265 B1 | 6/2001 | Cronk et al. | | |
| 6,322,590 B1 * | 11/2001 | Sillers et al. | | 623/10 |
| 6,454,803 B1 | 9/2002 | Romo, III | | |
| 6,971,388 B1 | 12/2005 | Michaels | | |
| 7,582,089 B2 * | 9/2009 | Schiebler | | 606/74 |
| 7,947,076 B2 * | 5/2011 | Vassallo et al. | | 623/10 |
| 2002/0173848 A1 * | 11/2002 | Sachs | | 623/10 |
| 2006/0276817 A1 * | 12/2006 | Vassallo et al. | | 606/185 |
| 2008/0027480 A1 * | 1/2008 | van der Burg et al. | | 606/199 |
| 2008/0077240 A1 * | 3/2008 | Saidi | | 623/10 |

OTHER PUBLICATIONS

Howard D. Stupak, 'Endonasal Repositioning of the Upper Lateral Cartilage and the Internal Nasal Valve', Annals of Otology, Rhinolgy and Laryngology 120(2):88-94.

(Continued)

*Primary Examiner* — Darwin Erezo
*Assistant Examiner* — Steven Ou
(74) *Attorney, Agent, or Firm* — Brenna K. Legaard; Lane Powell PC

(57) ABSTRACT

A device comprising a plate with attached suture including a portal and possibly including a fastener for the suture which can be used to dynamically reposition nasal cartilage to repair upper lateral cartilage, to splint septal cartilage, or to aid in scar inhibition in wound closure.

5 Claims, 6 Drawing Sheets

OTHER PUBLICATIONS

Jeevan B. Ramakrishnan, MD, Christopher J. Danner, MD, and Suzanne W. Lee, MD; *The use of porous polyethylene implants to correct nasal valve collapse*; Otolaryngology—Head and Neck Surgery (2007) 136, 357-361.

Judy Lee, MD, W. Matthew White, MD, Minas Constantinides, MD; *Surgical and Nonsurgical Treatments of the Nasal Valves*; Otolaryngol Clin N Am 42 (2009) 495-511.

Michael Friedman, MD, Hani Ibrahim, MD, George Lee, BS, and Ninos J. Joseph, BS, '*A Simplified Technique for Airway Correction at the Nasal Valve Area*', Otolaryngol—Head and Neck Surgery (2004) 131, 519-24.

Robert W. Dolan, 'Minimally Invasive Nasal Valve Repair, An Evaluation Using the NOSE Scale', Arch Otolaryngol Head Neck Surg. 2010;136(3):292-295.

* cited by examiner

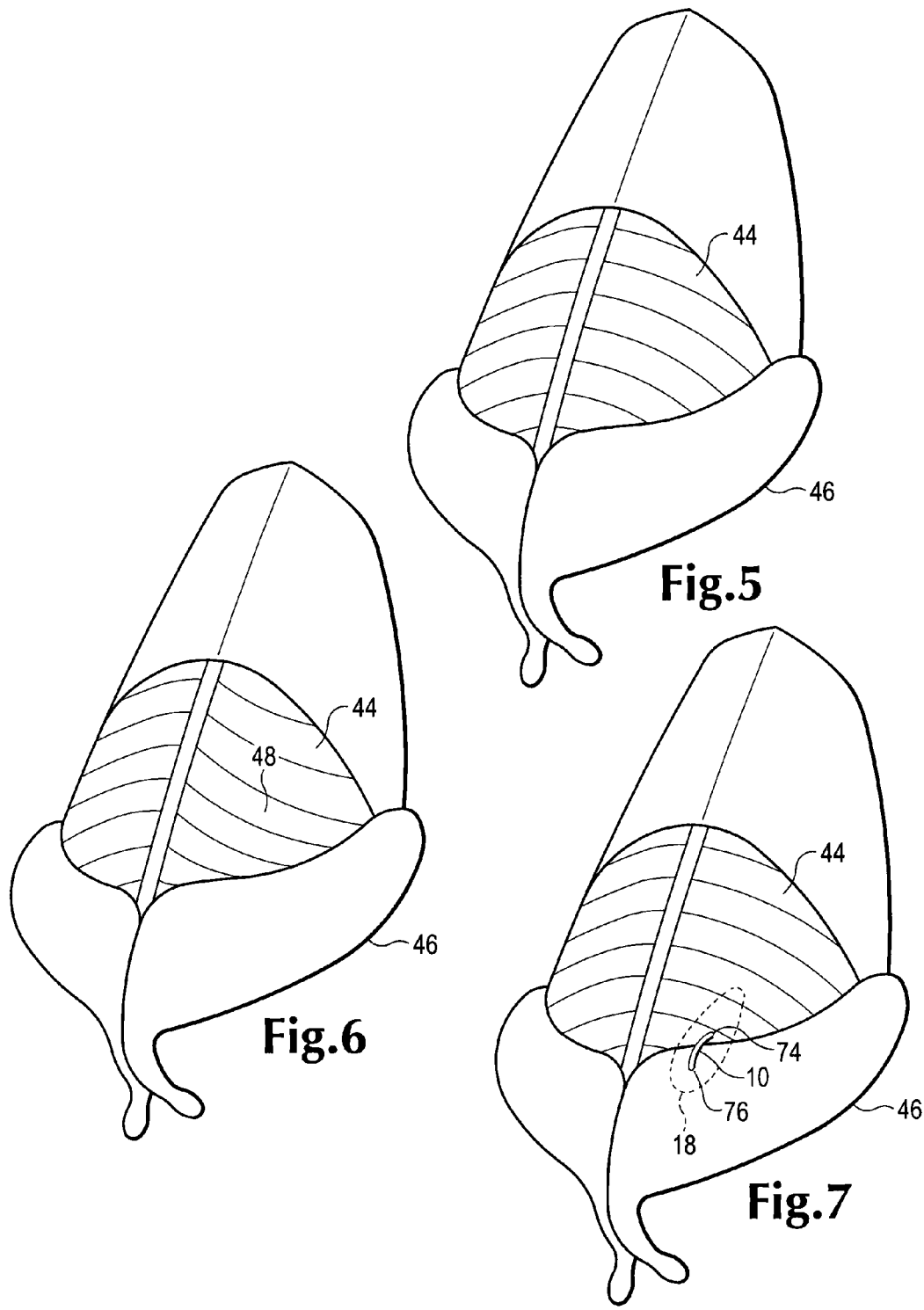

US 8,267,962 B2

DEVICE FOR REPOSITIONING CARTILAGE AND METHOD OF USE

Applicant claims the benefit of provisional applications 61/005,158 filed Dec. 3, 2007, 61/011,026 filed Jan. 14, 2008, and 61/070,646 filed Mar. 25, 2008.

BACKGROUND OF THE INVENTION

A cartilage repositioning device that can be utilized in nasal airway and aesthetic reconstructive procedures and surgeries of the nose and method for use are disclosed. The cartilage repositioning device disclosed may repair, partially restore, or restore the anatomic position of a collapsed or insufficient upper lateral cartilage, opening the internal nasal valve and causing a permanent repositioning of the upper lateral cartilage even after the device is removed.

When the upper lateral cartilages (ULC) collapse or are insufficient, the associated internal nasal valve (INV) can be impinged, which impairs breathing and causes cosmetic problems. Internal nasal valve dysfunction is a common condition. A damaged upper lateral cartilage and its associated dysfunctional internal nasal valve may be due to prior nasal surgery, trauma, congenital deficits, or simply insufficiency due to an individual's genetic makeup.

Various treatments of compromised upper lateral cartilage and its associated internal nasal valve dysfunction have been described and tested. However, these treatments either involve surgical cartilage grafting, which is invasive, requiring an extensive rhinoplasty, and may not be effective, or they involve removable devices which do not repair the collapsed cartilage.

Endogenous cartilage grafts (commonly referred to as "spreader" or "onlay" grafts) are currently the gold standard in the repair of the insufficient upper lateral cartilage and internal nasal valve. While somewhat effective, these procedures require cartilage harvesting from elsewhere in the body and a major rhinoplasty procedure to undermine the skin or lining of the nose to adequately place these grafts. Even after extensive procedures, aesthetic and functional success is not achieved in many cases.

The prior art has multiple surgical and nonsurgical devices which essentially deal with the nasal valve. These devices are commonly referred to as nasal dilators. The adhesively mounted external dilator disclosed in Johnson, U.S. Pat. No. 5,476,091, marketed as the BreatheRight™ Strip is an adhesive strip placed on the outer skin of the nose that, due to the recoil action of a support structure within the strip pulls open the nasal valve from an external position. The disadvantages of this device are that repeat placement is required for each use, and it is by definition noticeable on the external skin of the nose.

The surgically implantable nasal dilator disclosed by Hurbis, U.S. Pat. No. 6,106,541, the surgically implanted external nasal valve batten disclosed by Romo, U.S. Pat. No. 6,454,803, and the nasal valve apparatus disclosed by Vassallo, U.S. patent application Ser. No. 11/144,354, sought to improve on the permanence and noticeability of the external nasal dilator. These implants require no cartilage harvesting as required for spreader or onlay grafts. However, permanent surgical implants placed in soft tissue, particularly the thin soft-tissue envelope of the nose, have long-term significant risks. Over the lifetime of a patient, all surgical implants have a potential to become infected or even to extrude through the skin of the nose or migrate and become misplaced. The hardware can eventually breakdown over time. In addition, as with grafting, a major surgical procedure (usually open rhinoplasty) is required for implantation. Furthermore, one of the implants, the external nasal valve batten implant, addresses only problems with the external nasal valve, and not the challenging internal valve as in the present device.

Multiple internal nasal dilators including most recently the internal nasal dilator filter disclosed in Michaels, U.S. Pat. No. 6,971,388 have been described as well. These devices are largely dismissed by many clinicians due to their inconvenience. Like external dilators, they are not permanent, and must be applied before each use. Because they remain inside the nasal cavity, long-term usage can irritate and erode the internal nasal lining, creating chronic problems. In addition, most have some external component for security that is cosmetically noticeable and aesthetically unappealing. Finally, these devices also may interfere with the normal function of the nasal respiratory lining or mucosa.

Surgical splints for use after straightening procedures of the nasal septum, another component of the internal nasal valve, such as Doyle, U.S. Pat. No. 3,935,859, are known. These splints are sutured on both sides of the nasal septum at the conclusion of the septoplasty procedure in order to stabilize the reduced septum and to prevent hematoma formation. Guastella, U.S. Pat. No. 5,931,799 introduced a wing of a septal splint which would additionally splint the outer portion of the nasal valve. The purpose of said wing is proposed to splint the nasal valve after nasal surgery and to prevent scarring or stenosis of this area. This wing is not intended to suture and subsequently buttress a collapsed upper lateral cartilage into a restored position. In addition, because of its cumbrous size and attached wings, this prior device may be uncomfortable for the patient at the time of removal and/or placement.

SUMMARY OF THE INVENTION

A first aspect of the invention is a device for positioning and affixing cartilage comprising a plate having a first surface and a second surface, said device including a suture having a free end, said suture extending away from said first surface of said plate, said plate further including a portal for receiving said free end of said suture and directing said suture from said first surface to said second surface such that tension on said free end of said suture draws said suture toward said first surface of said plate.

In a further aspect of the invention, a device for approximating soft tissues comprising a flexible plate and attached suture, said plate having a first surface and a second surface, said plate having a portal for receiving said suture and passing it from said first surface to said second surface, said plate further having a fastener capable of knotless affixing said suture to said second surface is disclosed.

Also disclosed is a method of repositioning collapsed upper lateral cartilage, comprising providing a plate, said plate having a suture extending therefrom at a point of extension, a portal for receiving said suture, and a distance A between said portal and said point of extension, entering the collapsed upper lateral cartilage with said suture at a point of entry and exiting lower lateral cartilage with said suture at a point of exit, wherein the distance between said point of entry and said point of exit is approximately equal to distance A, and using said plate to exert pressure against said upper lateral cartilage.

Another aspect of the invention is a method of dilating a collapsed inner nasal valve comprising providing a plate having a first surface and a second surface, a suture having a free end extending from said first surface, said plate further including a portal for receiving said free end of said suture and directing said suture from said first surface to said second surface such that tension on said free end of said suture draws said suture toward said first side of said plate, passing said suture through the upper lateral cartilage and the lower lateral cartilage of a nose, passing said free end of said suture through said portal, and pulling on said suture and causing said plate to exert pressure against said upper lateral cartilage.

The foregoing and other objectives, features, and advantages of the invention will be more readily understood upon consideration of the following detailed description of the invention taking in conjunction with the accompanying drawings.

BRIEF DESCRIPTION OF THE DRAWINGS

FIG. 5 is a cut-away perspective view of the nose, with only the structures below the skin visible, with parallel lines marking the ULC.

FIG. 6 is a cut-away perspective view of the nose, with only the structures below the skin visible, with parallel lines marking the collapsed or insufficient ULC on the patient's left side.

FIG. 7 is a cut-away perspective view of the nose, with only the structures below the skin visible, with parallel lines marking the ULC restored to its expanded position by the plate, revealed with a dotted line on the undersurface of the junction of the ULC and LLC.

DETAILED DESCRIPTION OF THE PREFERRED EMBODIMENTS

Figure 1:
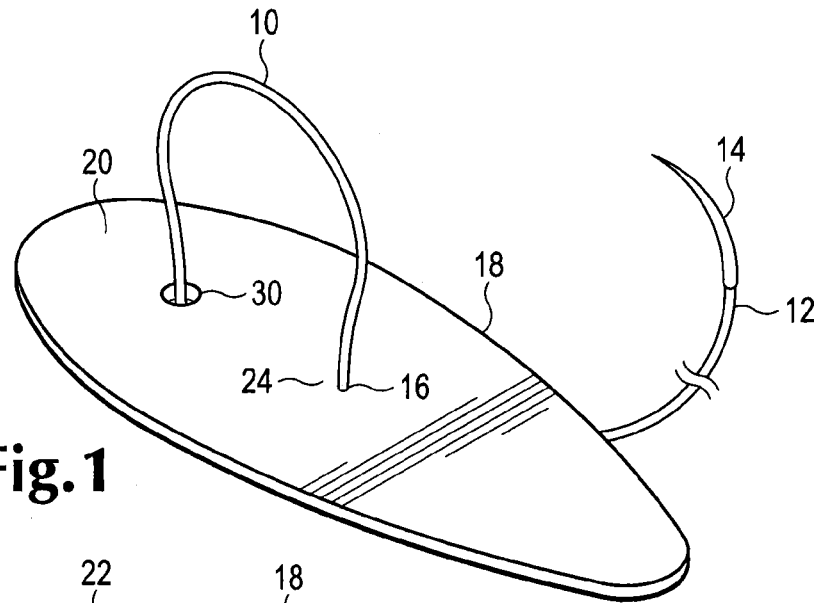
FIG. 1 is an enlarged perspective top-down view of the plate.

It is conventionally believed that the shape or position of cartilage cannot be modified without the addition of more cartilage, such as through a grafting procedure using cartilage from elsewhere in the body. Consequently, conventional alteration of the shape or position of the upper lateral cartilage in order to repair a compromised internal nasal valve involves either a nasal dilator which temporarily moves cartilage into a different position, but which change is reversed upon removal of the device, or a more permanent repair through a cartilage graft.

However, the inventor of the device and method disclosed herein was surprised to discover that the thin cartilage of the nasal envelope such as the upper lateral cartilage can heal into a different position without grafting if an opportunity for scar tissue development is provided and a dynamic device is used to reposition the cartilage and maintain the new position long enough for scar tissue to form. The inventor made this discovery when he was faced with a patient with insufficient upper lateral cartilage who had suffered four failed attempts by others to repair his nose through conventional grafting techniques. The inventor believed that another graft was likely to fail, and decided to try something new. He decided to attempt to dynamically reposition the cartilage and then allow scar tissue to affix it in its new location, even though it is conventionally believed that such a repair would not work. To his surprise, he discovered that a device which dynamically lifts upper lateral cartilage to at least the level of the lower cartilage while the position of the lower cartilage is maintained, then secures the cartilage while scar tissue forms, can repair an insufficient upper lateral cartilage. The device may be removable, because a device which is permanently implanted in the nose can cause irritation and erosion of the nasal lining. Moreover, it must fairly precisely position the cartilage. For example, if the device pulled the upper lateral cartilage and the lower lateral cartilage together so as to cause them to overlap one another, it would cause a cosmetic deformity called an alar retraction. For that reason, the inventor discovered that the upper lateral cartilage and lower lateral cartilage cannot simply be sutured together. Rather, a device which creates tension in an appropriate direction and location, and maintains an ideal spatial relationship between the cartilages during application of tension, is desirable. Because the device must maintain these spatial relationships during application of tension as well as maintain them during healing, the device must be capable of dynamically positioning as well as immobilizing tissue, and should be easily removable once healing is complete.

The device and method disclosed herein improve the function and aesthetic appearance of a damaged or insufficient upper lateral cartilage and internal valve of the nose utilizing a simple, office-based procedure, and a device which does not require permanent implantation. The device dynamically repositions cartilage by supporting previously collapsed upper lateral cartilage in proximity to intact lower lateral cartilage so that it heals in its new position.

Referring now to the drawings which form a part of this disclosure, in FIGS. 1-4, suture 10 is shown with a curved needle 14 on its free end 12 and opposite end 16 extending from plate 18. In this embodiment, the plate should be small, flat, thin, and oblong or approximately rectangular. Ideally it will be less than 2 mm thick. It may be composed of a stiff but resilient material. The suture extends from the top surface of the plate, may be fastened to the top surface 20 of the plate 18, or may be fastened to the bottom surface 22 of the plate 18 and extend through a hole in the plate in order to extend from the top surface 20 of the plate. The suture may extend from or be attached to the approximate center 24 of the plate. The suture 10 may be composed of permanent material like silk, nylon, or bio-resorbable substances. The plate 18 may be made of various materials, from bio-inert synthetic materials commonly used in nasal surgery such as hard-grade reinforced silicone, polyvinyl chloride, or made of bioresorbable rigid materials including polyglycolic acid. The broad flexibility allowed with the material is permitted as the device need not be implanted into the nasal soft tissue, but only remains in the nasal cavity until removal or absorption.

In the embodiment shown in FIGS. 1-4, the forward or anterior area of the plate 26 includes a portal 28 such as an eyehole 30 capable of receiving the needle 14 and suture 10 after they have been passed through cartilage layers.

Figure 2:
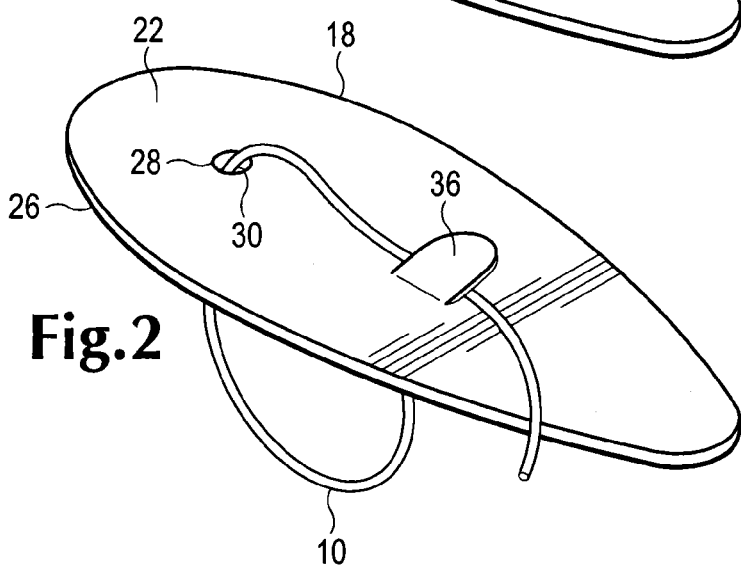
FIG. 2 is an enlarged perspective bottom view of the plate with distal end of the suture fastened into position.
Figure 3:
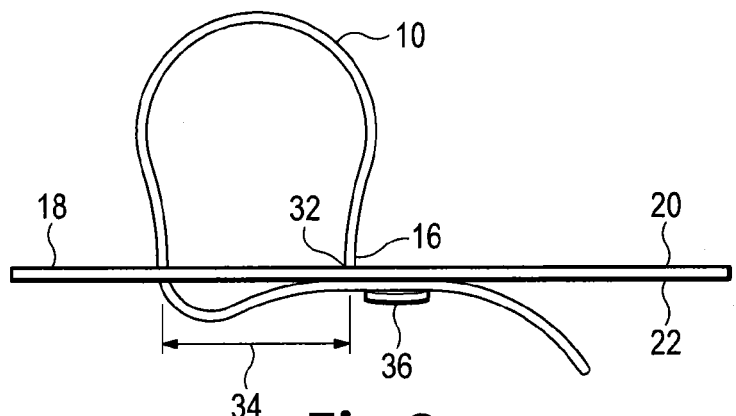
FIG. 3 is an enlarged side view of the plate with distal end of the suture fastened into position.

The plate 18 may also include a suture fastener 36. In the embodiments shown in FIGS. 1-4, the fastener 36 is located on the bottom surface 22 of plate 18. The fastener 36 may consist of a raised rigid flap comprised of a portion of plate 18 or a cleat on plate 18, and may knotlessly fasten the suture to the plate. In FIG. 2, the fastener is shown as broad and rounded into a near semi-circle although it may be another shape and located elsewhere on the bottom surface 22 of the plate 18. In the space between the fastener 36 and the plate 1 8 exists a narrow angle 40 that the suture 10 may be wedged into to lock it into a stable position. The bottom surface of the fastener 36 may have ridges or teeth that will assist in gripping and locking the passed suture 10. The fastener 36 may be angled with its opening facing away from the nasal airflow, to allowed continued aerodynamic nasal airflow with the implant in place. Because the airflow is different on the right and left sides of the nose, right and left versions of the device with appropriate angulation may be produced. The fastener may be made of the same or a different material than the plate is. For example, the fastener may be made of metal even if the plate is not made of metal.

Figure 8:
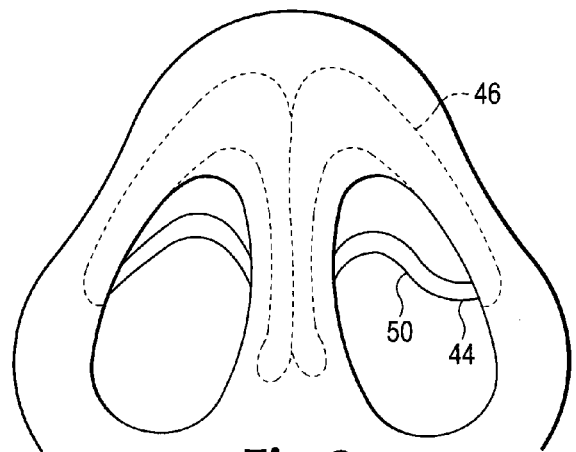
FIG. 8 is a base or bottom view of the nose, looking inside the nostrils, with the ULC and LLC visible through the skin and the patient's collapsed left ULC visible.

A candidate for this procedure can be identified from a history and physical examination. Patients with collapse of the upper lateral cartilage 44, as shown in FIG. 6 manifesting as having depressions in the middle one-third of the nose 48 on one or both sides, as shown in FIG. 6, or evidence of narrowing 50 at the internal nasal valve 52 as shown in FIG. 8, are the ideal candidates for this procedure. A structurally intact lower lateral cartilage 46 is also required. The ability of the upper lateral cartilage 44 to re-expand in a particular patient can be tested by internally opening the internal nasal valve with a cotton-tipped applicator, or stretching the skin adjacent to the nose in a lateral direction, with resultant subjective improvement in breathing.

Figure 9:
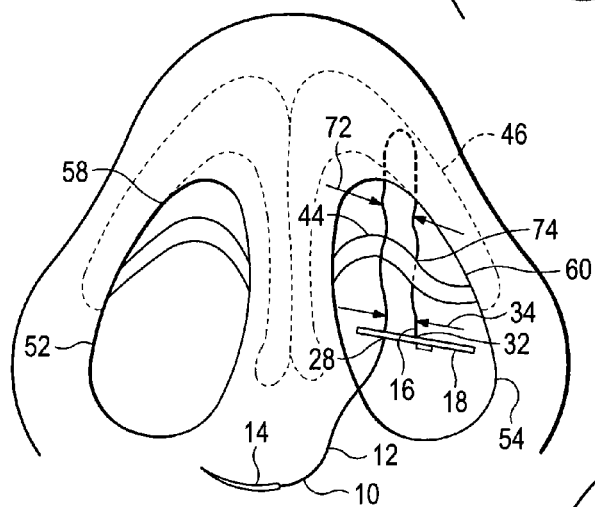
FIG. 9 is a base or bottom view of the nose, looking inside the nostrils, with the ULC and LLC visible through the skin, showing the plate within the nasal passage, after the suture and needle have passed through the ULC and LLC.

The procedure itself begins with appropriate anesthesia for the patient. In an office setting, with an awake patient, topical and injected anesthesia should be all that is required. Referring to FIG. 9, a standard unilateral incision is made into the membrane 58 between the upper lateral cartilage and lower lateral cartilage through an intra-nasal approach, with endoscopic or head-light guidance. Limited undermining of the skin 60 over the lower portion of the upper lateral cartilage is performed to encourage the formation of scar tissue that will fasten the cartilage into its new position following healing. The area of maximal interior nasal valve narrowing or upper lateral cartilage collapse is identified.

Figure 10:
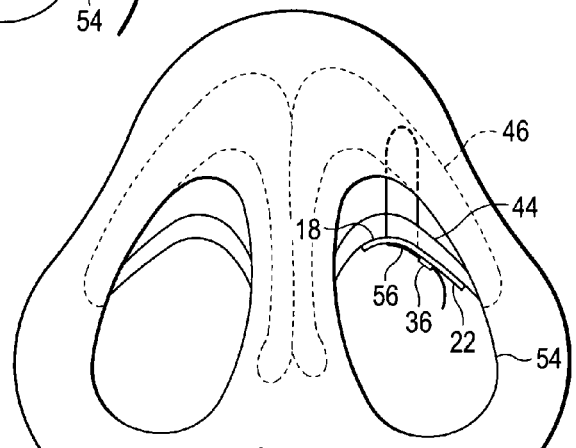
FIG. 10 is a base or bottom view of the nose, looking inside the nostrils, with the ULC and LLC visible, the ULC restored to its normal position by the plate and suture under proper tension, with suture fastened into position.

The needle 14 and suture 10 and plate 18 are introduced into the nasal cavity. As shown in FIGS. 9-10, after an intra-nasal or endoscopic approach and limited incision, the needle and free end 12 of the suture 10 are passed through the collapsed upper lateral cartilage 44 and sutured to the cephalic border of an intact lower lateral cartilage 46. As shown in FIG. 9, the curved needle 14 is speared through the maximally collapsed lower border of the upper lateral cartilage 44, from mucosal or lining side, to the undermined dorsal surface. The needle is regrasped, and then passed through the superior border of the lower lateral cartilage 46 at the incision site, with care taken to pass through a significant amount of the substance of the lower lateral cartilage 46, while avoiding penetrating into the nasal external skin. The needle 14 and suture 10 then may be passed through the portal 28 in the plate 18, which subsequently serves as a second point of fixation.

As shown in FIGS. 9 and 10, downward tension upon the free end 12 of the suture 10 raises the plate 18 as a flag is raised on a flagpole by the halyard, using the lower lateral cartilage 46 as the pulley. Once pulled into the nasal cavity 54 the plate 18 is maneuvered into position at the junction of the upper lateral cartilage 44 and lower lateral cartilage 46, and presses against the upper lateral cartilage 44 by virtue of the tension on the suture 10. The plate 18 exerts pressure against the upper lateral cartilage 44, repositioning it so as to open the internal nasal valve 52. The suture 10 may then be fastened to the plate 18, knotted, or in some other way prevented from being pulled back through the portal 28. It may be attached to the bottom surface 22 of the plate 18 with a fastener 36 adapted to secure the suture, excess free end 12 of suture 10 may be removed. FIGS. 7 and 10 show the plate in position.

Figure 4:
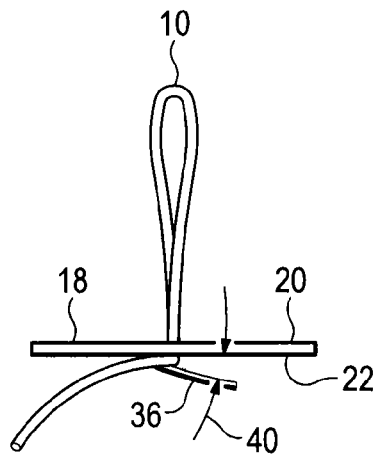
FIG. 4 is an enlarged end view of the plate with distal end of the suture fastened into position.
Figure 4A:
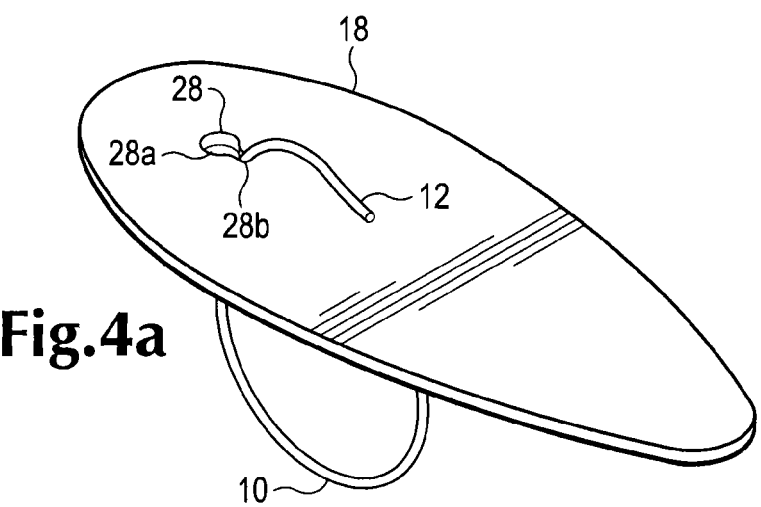
FIG. 4a is an enlarged perspective bottom view of the plate with a suture-affixing portal.
Figure 4B:
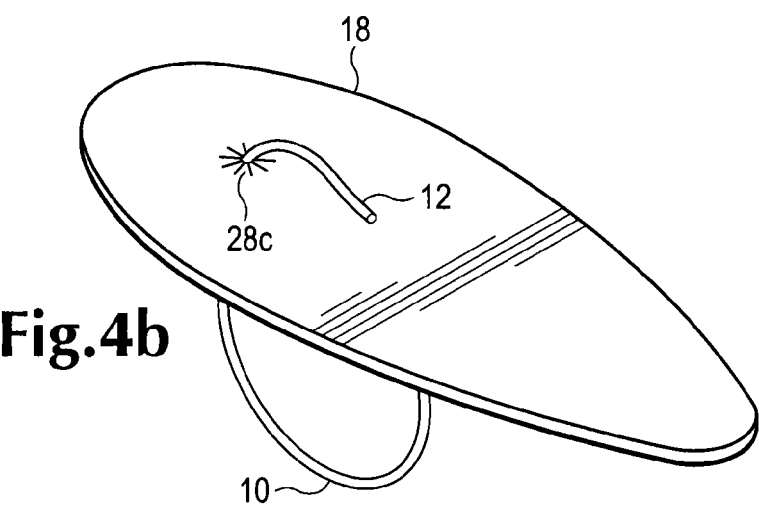
FIG. 4b is an enlarged perspective bottom view of the plate with an alternative suture-affixing portal.

The desired level of tension is kept on the free end 12 of the suture 10, as it is attached to the fastener 36 to secure the suture 10 and the position of plate 18. For additional security, a second fastener, not shown, may be used as well. For example, the second fastener may be a v-shaped cut-out in the plate or may be a metal component fastened to the plate. Additionally or alternatively, an additional suture may extend from the bottom surface 22 of the plate 18, and may be used to tie the suture 10 in order to affix it to the bottom surface 22 of the plate 18. The portal 28 may be used to affix the suture to the plate 18. This may be accomplished in a variety of ways. By way of example, as shown in FIG. 4a, the portal 28 may be teardrop or key hole shaped, composed of a wider area 28a and a narrower area 28b. The free end of the suture 12 is passed through the wide area 28a, then wedged into the narrower area 28b, where it is trapped and thus affixed to the plate 18. Alternatively, the portal can have inwardly directed elements 29c as shown in FIG. 4b which permit the free end of the suture 12 to pass through the portal, but which then catch on the suture material and prevent the suture from being pulled back through the portal. The portal may affix the suture to the plate with the aid of a knot in the suture or without use of a knot. An eyehole may be sized to permit the passage of suture but may still be small enough to prevent the suture from being pulled back through it.

The distance 34 between the portal 28 and the point of extension or attachment 32 of the attached end of the suture 16 should be approximately equal to the distance 72 between the needle's point of entry 74 in the upper lateral cartilage 44 and the point of entry 76 in the lower lateral cartilage 46. This distance may vary, but may typically be approximately 6-8 mm. If the distance 34 is significantly smaller than the distance 72 then the upper lateral cartilage and the lower lateral cartilage will be pulled together so as to overlap one another after the repair, and a cosmetic deformity called alar retraction will occur. If the distance 34 between the point of attachment of the suture and the portal is substantially larger than the distance 72 between the cartilages the upper lateral cartilage may not be positioned correctly for the repair to occur. For the same reasons, the plate functions as a bridge between compromised tissue and structurally intact tissue, ensuring that the points of exertion of tension are appropriately placed.

The plate 18 may be flat but resilient so that tension exerted by the suture 10 causes the plate to bow slightly 56 as shown in FIG. 10 so that it is concave when viewed from inside the nostril. This slight bowing creates a slight angulation, which accommodates the separation of the upper lateral cartilage and lower lateral cartilage inside the nasal cavity that even when approximated would not be a straight plane. The bowing helps allow approximation without over-correction.

Once healing occurs in several weeks, the device and its suture can be completely removed or bio-resorbed. This avoids both the implantation risks of a permanent implant (infection and extrusion), and the chronic irritation and maintenance required of a typical internal or external dilator. In addition, its placement requires only a minor procedure done either endoscopically or under operator headlight guidance.

An immediate benefit to the nasal airway should be seen and felt. Aesthetic improvement may be difficult to assess initially due to temporary edema of the skin.

In addition to the upper lateral cartilage, the other key anatomic components of the internal nasal valve include the nasal septum 62. Septal deviation is thus an additional cause of narrowing of the internal nasal valve. Using a modification of the present invention, the septum 62 may be stabilized and splinted after septoplasty. This procedure does not replace the septoplasty procedure, but just enhances the results in a simple fashion.

Figure 11:
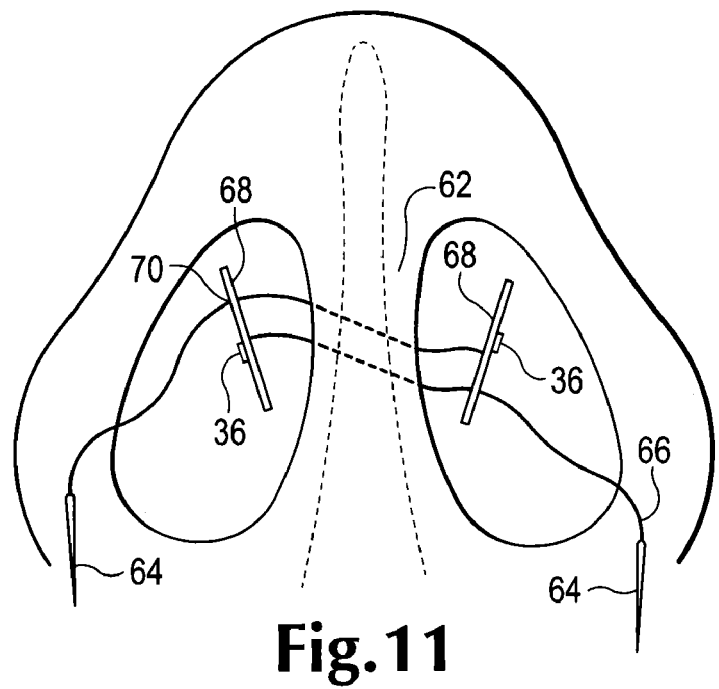
FIG. 11 is a base or bottom view of the nose, looking inside the nostrils, with the septal cartilage visible through the skin and two needles which have traversed the septum, fed through the portal of the plate on the opposite side of the nose.
Figure 12:
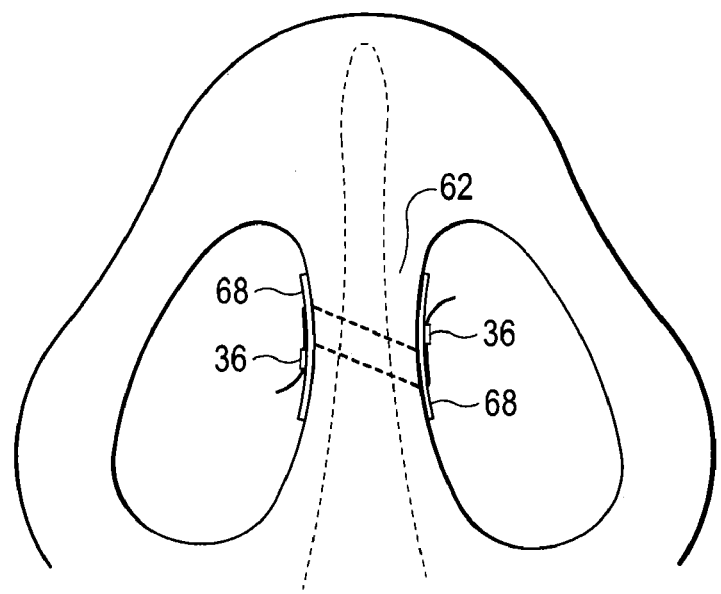
FIG. 12 is a base or bottom view of the nose, looking inside the nostrils, with the septal cartilage visible through the skin and the plates in position buttressing the septum.

A similar plate 68 may be used for this procedure. As shown in FIGS. 11-12, the plate may be larger, and a straight instead of a curved needle 64 may be used. As shown in FIG. 11, in addition, two of the devices, including 2 sutures and needles may be used.

At the conclusion of a standard septoplasty procedure, the lining flaps of the nasal skin remains loose and unapproximated. To reapproximate the flaps together in the midline, the device disclosed herein may be used. A straight needle 64 with suture 66, harnessed to a plate 68 is passed completely through the septum 62 to the opposite nasal cavity. An identical device is used from the opposite side as well. Once passed through the septum 62, the two needles are passed through their respective portals 70, and tension is subsequently applied to these needles 64. The plates sandwich the septum 62 between them as shown in FIG. 12, and each suture is then affixed to the opposing plate 68 by a fastener 36.

An additional use for the device disclosed herein and variations thereof is scar prevention in wound closure. The use of silicone sheeting in wound closure can reduce hypertophic, keloid, and other scars. While conventional use of silicone sheets and gels for scar reduction purposes teaches that the silicone should be placed after suture removal, the skin has already sealed at this point, and scarring may have already begun to develop. The device herein may be used to combine suturing with silicone sheeting, and thus may more effectively inhibit scarring.

The present device may be used in scar prevention in delicate scar revision or flap surgery, not simply to aid in closure of difficult high tension wounds. Unlike complex retention suture devices, the present device comprises a suture with a standard surgical needle on its free end, harnessed to a plate. The plate may include a portal such as an eyehole and a means of fastening the suture to the plate, such as a fastener for suture securing. The device is used to bring delicate tissue edges together, with tension distributed along the width of the plate instead of the very narrow width of the suture thread as with conventional suturing. The device in its preferred embodiment may be composed of a silicone sheet of an appropriate shape which may vary depending on the wound and anatomic site, designed to exert slight pressure on the healing wound, thus limiting scar progression. In addition, because of the portal fastener components, the suture may be secured without tying a knot, and can have its tension adjusted during the healing process. Because no suture tying is required, the device can be used for both external and endoscopic procedures where there is limited access to the surgeon for tying knots.

The procedure itself begins with appropriate anesthesia for the patient. Once adequate subcutaneous or submucosal stitches are placed if necessary, the device may be used. The device should be used instead of mucosal or cutaneous sutures, in areas where there may be a high risk for scarring or increased risk of vascular compromise to tissue, such as the corner of a rotational flap where maximal tension occurs, or where previous scars have already been excised.

Figure 13:
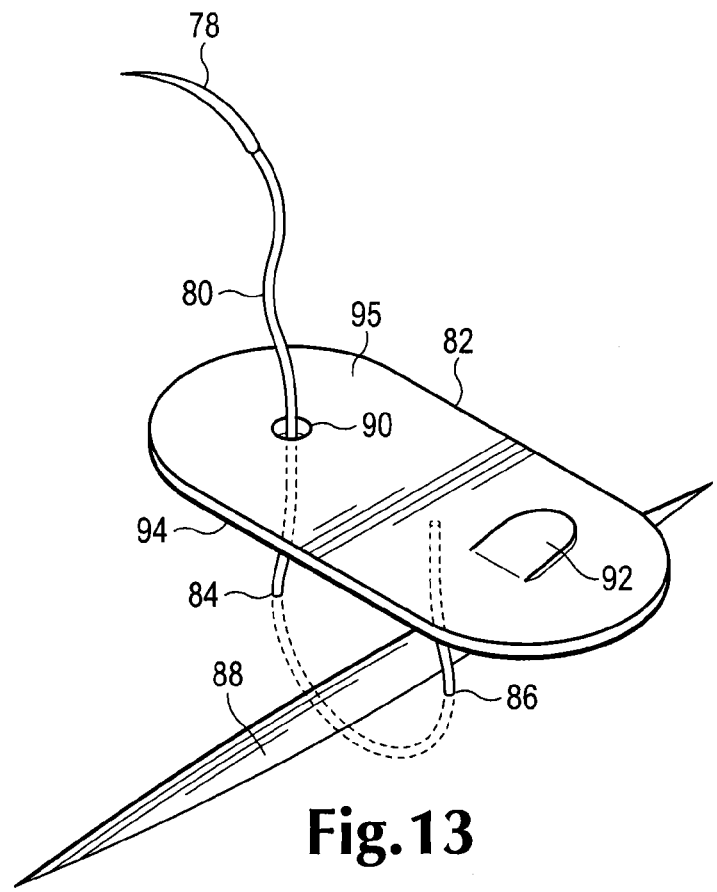
FIG. 13 is a perspective view of the device disclosed herein being used to close a wound.
Figure 14:
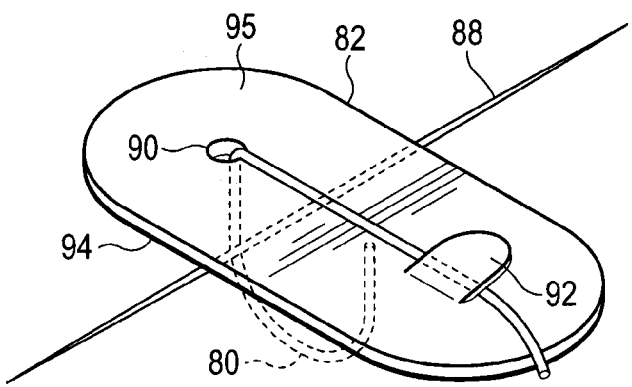
FIG. 14 is a perspective view of the device disclosed herein closing a wound.

Referring now to FIGS. 13 and 14, the needle 78 and suture 80 harnessed to the plate 80 is introduced into one edge 84 of the tissue, and subsequently passed through the opposite edge 86 through the wound 88 as in normal mucosal or dermal skin. Care must be taken to pass through a significant amount of the substance of the subdermal or submucosal tissue to permit adequate eversion and closure.

Once passed through, the needle 78 and suture 80 are pulled in a direction away from the tissue. Due to a "pulley" effect, the plate is subsequently urged toward the tissue and into position adjacent to the wound 88. Before the plate contacts the tissue, the needle and suture are fed through the portal 90, the needle and suture are pulled again, until the plate is maneuvered into position flush with the tissue plane, as shown in FIG. 14, the closed wound 88 at its midpoint (as a flag would be raised on a flagpole).

The wound closes just as the plate becomes flush with the tissue. The desired level of tension is kept on the needle end of the suture, and it is fed into the fastener 92 to secure its position and tension. For additional security, a second fastener, perhaps a v-shaped cut-out in the plate, may be used as well.

The plate can be removed at any point after healing, from days to weeks simply by unfastening the suture, and removing the plate from the tissue. Adhesive may be a feature on the distal ends of the plate. In this case, after release of the suture from the fastener, or during the healing process, the plate may exert its own closure forces, with any under-surface adhesive helping to hold the tissue in position.

Optional features are also possible on the plate. A single plate may have multiple sutures and their respective portals or cleats in parallel. This would allow one plate to cover a longer incision. The plate may be flat, curved, or oblong shape, depending on the tissue needing repair.

The terms and expressions which have been used in this specification are intended to describe the invention, not limit it. The scope of the invention is defined and limited only by the following claims.

I claim:

1. A method of repositioning a collapsed upper lateral cartilage, comprising:
    (a) providing a plate, said plate having a suture extending therefrom at a point of extension, and a portal for receiving said suture;
    (b) entering the collapsed upper lateral cartilage with said suture at a point of entry and exiting a lower lateral cartilage with said suture at a point of exit;
    (c) using said plate to exert pressure against said upper lateral cartilage from within a nasal cavity for a period of time sufficient to allow healing to substantially occur; and
    (d) subsequently removing said plate.

2. The method of claim 1 wherein said plate is semi-rigid.

3. The method of claim 1 wherein said plate is bioresorbable.

4. The method of claim 1 wherein said portal is a hole through said plate.

5. The method of claim 1 wherein said plate has a first surface and a second surface, and wherein said method further comprises the step of affixing said suture to said second surface with a fastener proximate to said second surface.

* * * * *